United States Patent [19]
Hines et al.

[11] Patent Number: 5,107,035
[45] Date of Patent: Apr. 21, 1992

[54] PROCESS FOR HIGH PURITY TETRABROMOBISPHENOL-A

[75] Inventors: Harold W. Hines, Emerson; Daniel A. Wood, Magnolia, both of Ark.

[73] Assignee: Ethyl Corporation, Richmond, Va.

[21] Appl. No.: 614,372

[22] Filed: Nov. 15, 1990

[51] Int. Cl.$^5$ .................... C07C 39/367; C07C 39/16
[52] U.S. Cl. .................... 568/726; 568/722; 568/723
[58] Field of Search .................... 568/726, 723, 722

[56] References Cited

U.S. PATENT DOCUMENTS

| | | | |
|---|---|---|---|
| 3,182,088 | 5/1965 | Hennis | 260/619 |
| 3,868,423 | 2/1975 | Montanari et al. | 260/619 A |
| 4,112,242 | 9/1978 | Swietoslawski et al. | 568/726 |
| 4,451,675 | 5/1984 | Bounds | 568/726 |
| 4,628,124 | 12/1986 | McKinnie et al. | 568/726 |
| 4,701,568 | 10/1987 | McKinnie et al. | 568/726 |
| 4,783,556 | 11/1988 | Mitchell et al. | 568/726 |

FOREIGN PATENT DOCUMENTS

| | | | |
|---|---|---|---|
| 2005259 | 2/1970 | Fed. Rep. of Germany | 568/726 |
| 949306 | 2/1964 | United Kingdom | 568/726 |

*Primary Examiner*—Werren B. Lone
*Attorney, Agent, or Firm*—David E. LaRose; Richard L. Hansen

[57] ABSTRACT

The quality of a product predominant in tetrabromobisphenol-A is enhanced by heat treating the product for a period of time and at a temperature which are sufficient to obtain a TBBPA predominant product having less than about 50 ppm of hydrohalide impurities.

8 Claims, No Drawings

PROCESS FOR HIGH PURITY TETRABROMOBISPHENOL-A

BACKGROUND

This invention relates to a process for enhancing the purity of a flame retardant product predominant in a tetrabromobisphenol-A.

4,4'-isopropylidenebis(2,6-dibromophenol) is a well known commercial flame retardant and is usually referred to as tetrabromobisphenol-A (hereinafter "TBBPA"). Products comprised predominantly of TBBPA are useful as flame retardants in many macromolecular formulations. The literature is replete with processes for the manufacture of TBBPA, see, for example, U.S. Pat. No. 3,234,289; U.S. Pat. No. 3,363,007; U.S. Pat. No. 3,546,302; U.S. Pat. No. 3,868,423; U.S. Pat. No. 3,929,907; U.S. Pat. No. 4,013,728; U.S. Pat. No. 4,036,894; and U.S. Pat. No. 4,701,568. Two process which produce a TBBPA predominant product having a particularly low organic impurity content are described in U.S. Pat. No. 4,628,124 and U.S. Pat. No. 4,783,556 incorporated herein by reference. While the processes described in the '124 and '556 patents yield products which are useful for most flame retardant applications, there exists a need for a TBBPA predominant product having both a low organic impurity and a low HBr impurity. These low impurity TBBPA predominant products have particular application as flame retardants in polymers and plastics for the electronics industry.

THE INVENTION

A process has now been discovered which greatly enhances the quality of a product predominant in tetrabromobisphenol-A, the process comprising heat treating the tetrabromobisphenol-A predominant product having impurities for a period of time and at a temperature which are sufficient to obtain a tetrabromobisphenol-A predominant product having less than about 50 ppm of a hydrohalide impurity.

The process of the present invention enables the production of a product predominant in tetrabromobisphenol-A (TBBPA) on a large scale at high yield having substantially lower hydrohalide and organic impurities. The invention has particular application in providing a means for enhancing the quality of a TBBPA predominant having a low organic impurity content. However, the process of this invention can be applied to a TBBPA predominant product produced by any number of prior art processes.

In another embodiment, this invention provides a flame retardant composition comprising a product predominant in tetrabromobisphenol-A and containing less than about 50 ppm a hydrohalide impurity and less than about 3.0 percent organic impurity.

The hydrohalide impurity which is present in the TBBPA product may be HBr, HCl, HI, HF, or mixtures thereof. Generally, the hydrohalide is HBr, or HCl or mixtures thereof.

A key feature of this invention is heat treating the TBBPA predominant product at a temperature and for a period of time which are sufficient to reduce the amount of hydrohalide impurity in the thus treated product. When heat treating the product, the temperature is generally above about 110° C. Preferably, the temperature is in a range of from about 120° C. to about 180° C., and most preferably in a range of from about 130° C. to about 175° C. Higher or lower temperatures may also be used. However, the temperature should not be so high as to cause melting or degradation of the TBBPA predominant product. At a temperature lower than the preferred temperature, a longer heating time may be required to achieve the desired results.

The time required to obtain the enhanced quality product is related to the temperature used for the heat treating. At a temperature above about 120° C., the time for heat treating the product is preferably greater than about 10 seconds. A preferred residence time for heat treating a product predominant in TBBPA ranges from about 30 seconds to about 1 hour with the most preferred time ranging from about 5 minutes to about 30 minutes.

The time required may also depend on the equipment selected for the heat treating process. Equipment which may be useful in the process of this invention include the Wyssmont Turbo-Dryer ® and the Bepex Torusdisc ® Dryer, e.g. Torusdisc Model TDJ2611 having 218 square feet of heat transfer area and a 26 minute residence time at about 120° C. and the like. Those skilled in the art can readily select heat treating equipment based on the above residence times and temperatures in order to obtain the desired low impurity product.

Pressure is not critical to the process of this invention as the bromination reaction can be carried out at pressures ranging from subatmospheric to superatmospheric. It is less costly and more desirable to operate at about atmospheric pressure.

A particularly preferred process for the production of a product predominant in TBBPA is described in Mitchell, et al., U.S. Pat. No. 4,783,556 incorporated herein by reference. The process of the Mitchell et al. patent produces a product generally having less than about 3 percent organic impurities. Typical organic impurities found in the product are partially brominated bisphenol compounds e.g. monobromobisphenol-A, dibromobisphenol-A and tribromobisphenol-A; partially brominated phenol compounds, e.g. bromophenol, dibromophenol, and tribromophenol; and brominated phenylphenols formed from traces of phenylphenol found in the bisphenol-A reactant. Traces of other organic compounds found in the TBBPA predominant product may include 1-bromo-2-(3,5-dibromo-4-hydroxyphenyl)-2-methoxypropane, 1,1-dibromo-2-(3,5-dibromo-4-hydroxyphenyl)-2-methoxypropane, and 1,3-dibromo-2-(3,5-dibromo-4-hydroxyphenyl)-2-methoxypropane.

While the organic impurities of the product produced by the Mitchell et al. process are acceptably low for most flame retardant applications, the hydrohalide impurity in the product is typically about 60 ppm or more. It has now been discovered that TBBPA predominant product containing a hydrohalide impurity which is initially about 60 ppm or more can be treated by the process of this invention to obtain a TBBPA predominant product having less than about 50 ppm and most preferably, less than about 30 ppm hydrohalide impurity. When produced by the process of the Mitchell et al. patent, the TBBPA predominant product treated by the process of this invention also contains less than about 3.0 percent organic impurity.

The process of this invention may be used to reduce the hydrohalide content of a TBBPA predominant product before or after drying the product. Preferably, the product to be treated by the process of this invention has been separated from the reaction mass and most preferably, the product has been dried and ground to a powder having an average particle size of about 70 microns or less.

The following examples illustrate the process of this invention.

EXAMPLE

One vent of a lab oven was removed and a stirrer having an inverted ½ moon paddle was inserted into the oven through the vent. A 600 mL beaker was placed into the oven and the beaker was preheated to about the oven temperature. TBBPA product (20 grams) produced by the process of the Mitchell et al. Patent, U.S. Pat. No. 4,783,556 placed into the preheated beaker which was in the oven and the product was stirred by hand during the heat treating process. The product had an initial HBr content of about 84 ppm. The results of the heat treating runs are listed in Table I. Samples 1-8 were previously dried before heat treating. Samples 9-10 were still wet with prior to heat treating and had an initial HBr content of 74 ppm.

TABLE I

| Run No. | Time (min.) | Temp. (°C.) | HBr (ppm) |
| --- | --- | --- | --- |
| 1 | 10 | 121-124[1] | 35 |
| 2 | 10 | 135-140[1] | 10 |
| 3 | 5 | 150-155[1] | 10 |
| 4 | 5 | 135[2] | 10 |
| 5 | 0.5 | 135[2] | 49 |
| 6 | 1.5 | 140[2] | 10 |
| 7 | 4 | 127[2] | 15 |
| 8 | 4 | 105[2] | 31 |
| 9 | 2.2 | 135[2] | 24 |
| 10 | 2.1 | 140[2] | 16 |

[1]Oven temperatures.
[2]TBBPA product temperatures.

In Runs 11-20, about 5 pounds of dry TBBPA predominant product produced by the process described in the Mitchell et al. patent, and initially containing about 59 to about 62 ppm HBr was dried at various temperatures in the dryers indicated. Samples of the product during the drying cycle were analyzed and the results are given in the following Tables II and III.

TABLE II

| Run No. | Temp. (°C.)[3] | Time (min.) | HBr (ppm) |
| --- | --- | --- | --- |
| Wyssmont Turbo-Dryer ® | | | |
| 11 | 121 | 10 | 58 |
| | | 15 | 55 |
| | | 20 | 50 |
| | | 25 | 46 |
| | | 30 | 35 |
| 12 | 132 | 10 | 53 |
| | | 14 | 49 |
| | | 18 | 42 |
| | | 22 | 35 |
| | | 26 | 27 |
| 13 | 143 | 10 | 51 |
| | | 14 | 48 |
| | | 20 | 26 |
| | | 30 | 14 |
| 14 | 160 | 10 | 44 |
| | | 14 | 33 |
| | | 20 | 18 |
| | | 30 | 11 |
| 15 | 143 | 18 | 50 |
| | | 30 | 22 |
| | | 40 | 13 |
| | | 60 | 10 |
| 16 | 177 | 10 | 48 |

TABLE II-continued

| Run No. | Temp. (°C.)[3] | Time (min.) | HBr (ppm) |
| --- | --- | --- | --- |
| | | 15 | 19 |
| | | 20 | 15 |
| | | 25 | 10 |
| | | 30 | 8 |

[3]Dryer air temperature.

TABLE III

| Run No. | Temp. (°C.)[3] | Time (min.) | HBr (ppm) |
| --- | --- | --- | --- |
| Bepex Torusdisc ® Dryer | | | |
| 17 | 149 | 5 | 49 |
| | | 9 | 41 |
| | | 11 | 34 |
| | | 18 | 21 |
| | | 31 | 20 |
| 18 | 177 | 3 | 39 |
| | | 6 | 22 |
| | | 10 | 17 |
| | | 50 | 14 |
| 19 | 163 | 6 | 29 |
| | | 8 | 19 |
| | | 12 | 15 |
| | | 22 | 19 |
| | | 30 | 11 |
| 20 | 149 | 3 | 47 |
| | | 5 | 32 |
| | | 10 | 24 |
| | | 13 | 20 |
| | | 15 | 15 |
| | | 30 | 12 |

[3]Dryer air temperature.

The process of this invention is applicable to flame retardant products comprised predominantly of brominated compounds derived from compounds represented by the following:

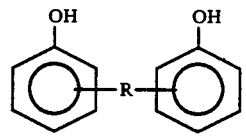

wherein R is a divalent aliphatic hydrocarbon group of 1-4 carbon atoms or a direct bond between two benzene rings. Representative examples are 4,4'-methylenebisphenol; 2,2'-methylenebisphenol; 2,4'-methylenebisphenol; 4,4'-ethylidenebisphenol; 2,2'-ethylidenebisphenol; 2,4'-ethylidenebisphenol; 2,2'-isopropylidenebisphenol; 2,4'-isopropylidenebisphenol; 4,4'-butylidenebisphenol; 2,2'-butylidenebisphenol; 4,4'-bisphenol; 2,2'-bisphenol; 2,4'-bisphenol and the like. These bisphenols can be substituted for the bisphenol-A, i.e., 4,4'-isopropylidenebisphenol, used in the foregoing description and examples of the present invention. All of the brominated products can be used as fire retardants in a broad range of organic materials normally susceptible to combustion in the presence of air and an ignition source.

Other variations are possible within the spirit and scope of the appended claims.

What is claimed is:

1. A process for enhancing the quality of a flame retardant product predominant in tetrabromobisphenol-A (TBBPA) which product initially contains about 60 ppm or more HBr impurity, the process comprising heat treating the TBBPA predominant product having said impurities for 30 seconds or more and a temperature above about 110° C. which time and temperature are sufficient to obtain a TBBPA predominant product having less than about 50 ppm of HBr impurity.

2. The process of claim 1 wherein the temperature is in a range of from about 130° C. to about 170° C.

3. The process of claim 1 wherein the time is in a range of from about 30 seconds to about 1 hour.

4. The process of claim 1 wherein the tetrabromobisphenol-A product to be heat treated is an essentially dry powder.

5. The process of claim 3 wherein the tetrabromobisphenol-A product to be heat treated is an essentially dry powder.

6. The process of claim 5 wherein the amount of HBr impurity in the heat treated product is less than about 30 ppm.

7. A flame retardant composition comprising a product predominant in tetrabromobisphenol-A and containing less than about 60 ppm HBr impurity and less than about 2.0 percent organic impurity.

8. The composition of claim 7 having less than about 30 ppm of HBr impurity.

* * * * *